United States Patent [19]

Pemberton et al.

[11] 4,224,410
[45] Sep. 23, 1980

[54] METHOD FOR ETHANOL FERMENTATION

[75] Inventors: Mark S. Pemberton, Shawnee, Kans.; Steven D. Crawford, Independence, Mo.

[73] Assignee: University of Arkansas Foundation, Fayetteville, Ark.

[21] Appl. No.: 966,936

[22] Filed: Dec. 6, 1978

[51] Int. Cl.$^2$ ............................ C12P 7/14; C12N 1/16
[52] U.S. Cl. .................................... 435/162; 435/165; 435/255; 435/921
[58] Field of Search .................... 195/33, 82, 83, 111; 435/161, 255, 921, 162, 165

[56] References Cited

U.S. PATENT DOCUMENTS 4,009,075  2/1977  Hoge .................................... 195/33

OTHER PUBLICATIONS

Journal of Fermentation Technology, vol. 53, No. 6, pp. 311–314 (1975).

Primary Examiner—Lionel M. Shapiro
Attorney, Agent, or Firm—Donald R. Cassady

[57] ABSTRACT

Fermentation of glucose and simultaneous-saccharification fermentation of cellulose using cellulose and a yeast are improved by utilization of the yeast *Candida brassicae*, ATCC 32196.

3 Claims, 5 Drawing Figures

METHOD FOR ETHANOL FERMENTATION

BACKGROUND OF THE INVENTION

This invention relates to an improved method for the manufacture of ethanol from cellulose. By the process of this invention a cellulose-containing substrate is reacted in one step with cellulase enzymes and with a means to manufacture ethanol.

The manufacture of ethanol from cellulose and cellulose-containing materials in one step has been disclosed and claimed in U.S. Pat. No. 3,990,944, Gauss, Suzuki, Takagi. Variations of the method have been claimed by Hoge in U.S. Pat. No. 4,009,075 and others.

Additionally, Metzger in U.S. Pat. No. 3,711,392 and Lang in U.S. Pat. No. 4,094,740 and U.S. Pat. No. 4,093,516 disclose the manufacture of ethanol from organic waste material.

Hoge discloses the use of *Saccharomyces cerevisiae* as the yeast useful for converting the glucose produced in situ into ethanol. Gauss et al. discloses the use of *Saccharomyces cerevisiae*, and *Rhizopus javanicus* for the same purpose. Neither of the Lang patents nor Metzger provide a disclosure of specific yeasts which will convert glucose to ethanol. Other yeasts which are well-known for their ability to convert glucose to ethanol include Baker's yeast and *Saccharomyces carlsbergensis*.

Amano, et al., "A Strongly Ethanol Assimilating New Yeast", The Society of Fermentation Technology, Japan, 53, 311 (1975) discloses the yeast *Candida brassicae*, IFO 1664, ATCC 32196, and its unique and unobvious differences from other well-known Candida species. According to Amano, et al., the following constitutes a description of *Candida brassicae*, ATCC 32196.

Cultura in extracto malti: add 25° C., post 3 dies cellulae ovoideae ad cylindricae, 2.5–5×3–17.5μ, singulares vel catenatae; pseudomycelium praesens. Sedimentum et pellicula formantur.

Cultura in striis agaro malti: add 17° C., post unum mensem color albidus ad flavalbidus, pagina opaca, elevata, mollis et laevis vel crispulata. Pseudomycelium praesens abundanter.

Ascosporae, ballistosporae et teliosporae nullae.
Fermentatio: glucosum.
Assimilatio originum carbinum: glucosum, galactosum, sucrosum, maltosum (valde exigue), raffinosum (exigue, D-xylosum (exigue), ethanolum, glycerolum, acidum lacticum et acidum succinicum.

Kalii nitras non assimilatur, arbutinum non finditur, ureum non finditur. Vitamina addita non necessaria sunt.

Temperatura maxima crescentiae 43°–45° C.
TYPUS: culture RIFY E-17 in collectione Research Institute of Fermentation, Yamanashi University, Kofu, isolata e flio *Brassica oleracea* var. *capitata* in Kofu, Japonia, 1973.

Growth in malt extract: After 3 days at 25° C., cells are short-oval to cylindrical, (2.5–5)×(3–17.5)μ, single, in pairs or in chains (FIG. 1). Pseudomycelical cells are formed (FIG. 2). A sediment and thin wrinkled pellicle are formed.

Growth on malt agar: After one month at 17° C., the streak culture is white to slightly yellowish, dull, raised, soft and smooth or slightly wrinkled.

Slide cultures on potato agar: A pseudomycelium with a tree-like formation is abundantly formed (FIGS. 3 and 4).

Formation of spores: No ascospore, ballistospore or teliospore is formed.
Fermentation:

| Fermentation: | | | |
|---|---|---|---|
| Glucose | + | Trehalose | − |
| Galactose | − | Lactose | − |
| Sucrose | − | Raffinose | − |
| Maltose | − | Xylose | − |
| Assimilation of carbon compounds: | | | |
| Glucose | + | D-Ribose | − |
| Galactose | + | L-Rhamnose | − |
| L-Sorbose | − | Ethanol | + |
| Sucrose | + | Glycerol | + |
| Maltose | vw | Erythritol | − |
| Cellobiose | − | Ribitol | − |
| Trehalose | − | Galactitol | − |
| Lactose | − | D-Mannitol | − |
| Melibiose | − | D-Glucitol | − |
| Raffinose | w | α-Methyl-D-glucoside | − |
| Melezitose | − | Salicin | − |
| Inulin | − | DL-Lactic acid | + |
| Soluble starch | − | Succinic acid | + |
| D-Xylose | w | Citric acid | − |
| L-Arabinose | − | Inositol | − |
| D-Arabinose | − | | |

Assimilation of potassium nitrate: Absent.
Growth in a vitamin-free medium: Good growth.
Sodium chloride tolerance: 14–15% (w/v).
Maximum temperature for growth: 43–45° C.
Splitting of arbutin: Negative.
Hydrolysis of urea: Negative.

SUMMARY OF THE DISCLOSURE

It has now been discovered that *Candida brassicae*, ATCC 32196, provides several new and unobvious advantages over the usual yeasts in transforming to ethanol the in situ glucose manufactured by saccharification of cellulosics in a simultaneous-saccharification fermentation reaction.

Thus, the method of Gauss, et al. is improved by the use of *Candida brassicae* in place of *Saccharomyces cerevisiae* or *Rhizopus javanicus*.

DETAILED DESCRIPTION

As described above and in the prior art cited herein relating to simultaneous-saccharification fermentation, this invention is characterized by simultaneously reacting a cellulase and an alcohol-producing microorganism upon a substrate made up of either cellulose or a substance composed preponderantly of cellulose.

The cellulosic substrates which are useful as starting materials for the present invention include purified cellulose, agriculturally produced materials such as cotton, wood, rice straw, wheat straw, maize ears (corn cobs) and other substances composed preponderantly of cellulose such as newspaper, corrugated paper, magazine paper and scrap paper. For these substances to be used effectively as substrates for the saccharification reaction in the presence of cellulase, it is desirable to pulverize or disintegrate them. For the hydrolysis of these cellulosic substrates, use of a commercially available cellulase will suffice. An enzymatic preparation such as, for example, Cellulase Onotsuga may be used. A liquid containing a cellulase, namely a culture liquid from a cellulase-producing microorganism such as, for example, a culture liquid from *Trichoderma reesei* QM9414 (*Trichoderma viride* QM9414) may also be used.

As the alcohol-producing microorganism to be simultaneously reacted upon the hexoses formed from the degradation of cellulose is the yeast *Candida brassicae*, ATCC 32196.

In order for the cellulose substrate to be simultaneously reacted upon by a cellulase and the *Candida brassicae*, an aqueous suspension containing from 1 to 30% by weight of cellulose or a substance composes predominantly of cellulose is prepared and thermally sterilized so as to serve as a substrate, a cellulase (or a cellulase-containing liquid) is added to the substrate and at the same time the *C. brassicae*, previously cultured, is added thereto so that the reaction will proceed anaerobically at temperatures of about 30°–45° C.

An additional benefit has been shown by the use of the organism *Candida brassicae*, ATCC 32196. Both during cultivation of the organism prior to inoculation into the simultaneous saccharification-fermentation and during fermentation alone and simultaneous saccharification-fermentation the organism grows to a greater biomass yield and more particularly to a greater cell count per unit of time than the usual yeasts for hexose-to-alcohol fermentation. Thus, cultivation of *C. brassicae*, ATCC 32196, in a nutrient medium at temperatures of 30°–45° C. provides more active cells for inoculation into the simultaneous saccharification-fermentation reaction mixture, and biomass residues are greater after fermentation or simultaneous saccharification-fermentation allowing for greater byproduct credits in the economics of manufacture of ethanol from cellulose. The biomass product is a nutritive animal feed of high protein value.

Further, high cell yields are realized over a broad temperature range. It has been found that exceptionally high cell yields can be grown at temperatures up to 42°–43° C., a temperature at which most yeasts will not propagate.

A better understanding and evaluation of the invention is provided by the drawings and the accompanying description which is to be considered as illustrative of, but not limiting on the invention.

In all the drawings the curves represent a reasonable interpretation of the activity shown as a function of the temperature at which the activity was observed. Curves were drawn to be illustrative of data accumulated and specific points are experimentally discovered values.

In each curve the specific points are demonstrated as follows:

Circles (O) *Candida brassicae* ATCC 32196
Triangles (△) *Saccharomyces cerevisiae* ATCC 4126
Crosses (X) *Saccharomyces cerevisiae* ATCC 4132
Squares (□) *Saccharomyces carlsbergensis* IAM 4787
Diamonds (◇) *Saccharomyces cerevisiae* ATCC 24858

FIGS. 3 and 4 demonstrate the added cell growth characteristics of *Candida brassicae*, ATCC 32196.

Figure 1:
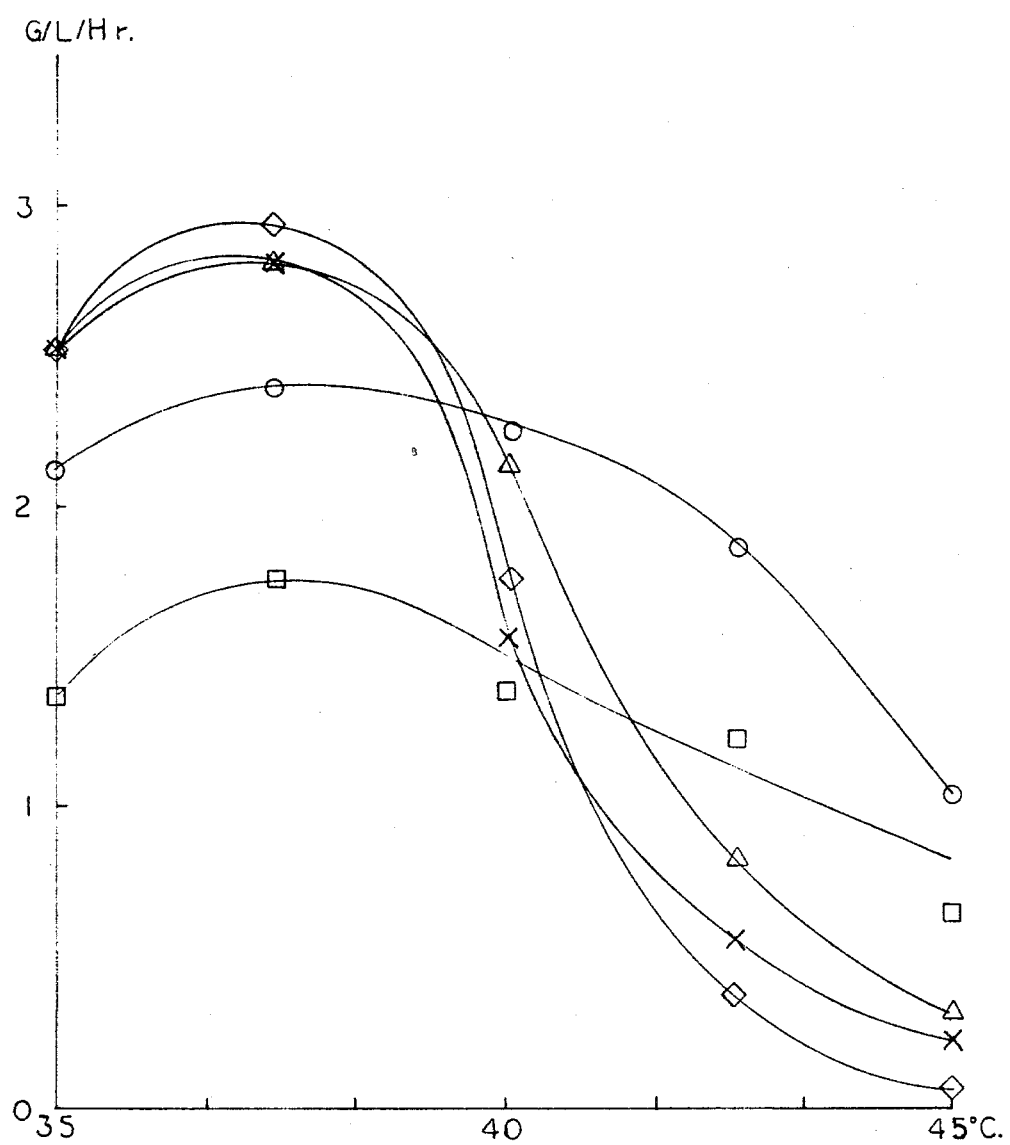
FIG. 1 represents the rate of formation of ethanol on a 24 hour period at the indicated temperature for various yeasts when grown in a 100 g/l glucose-containing medium comprising the usual growth ingredients.
Figure 2:
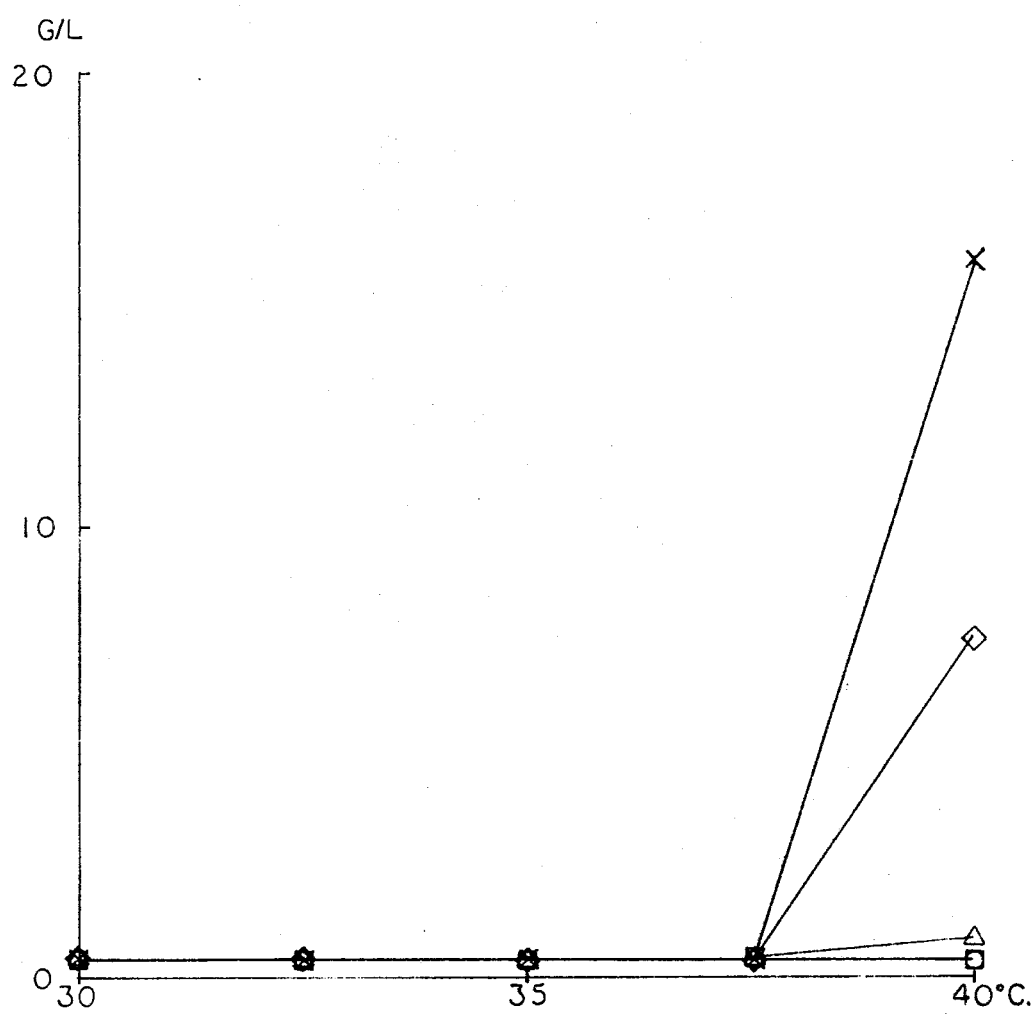
FIG. 2 represents the actual glucose concentration of a yeast culture growing in a nutrient medium containing 20 g/l of glucose 12 hours after inoculation and reaction at the various temperatures indicated.
Figure 3:
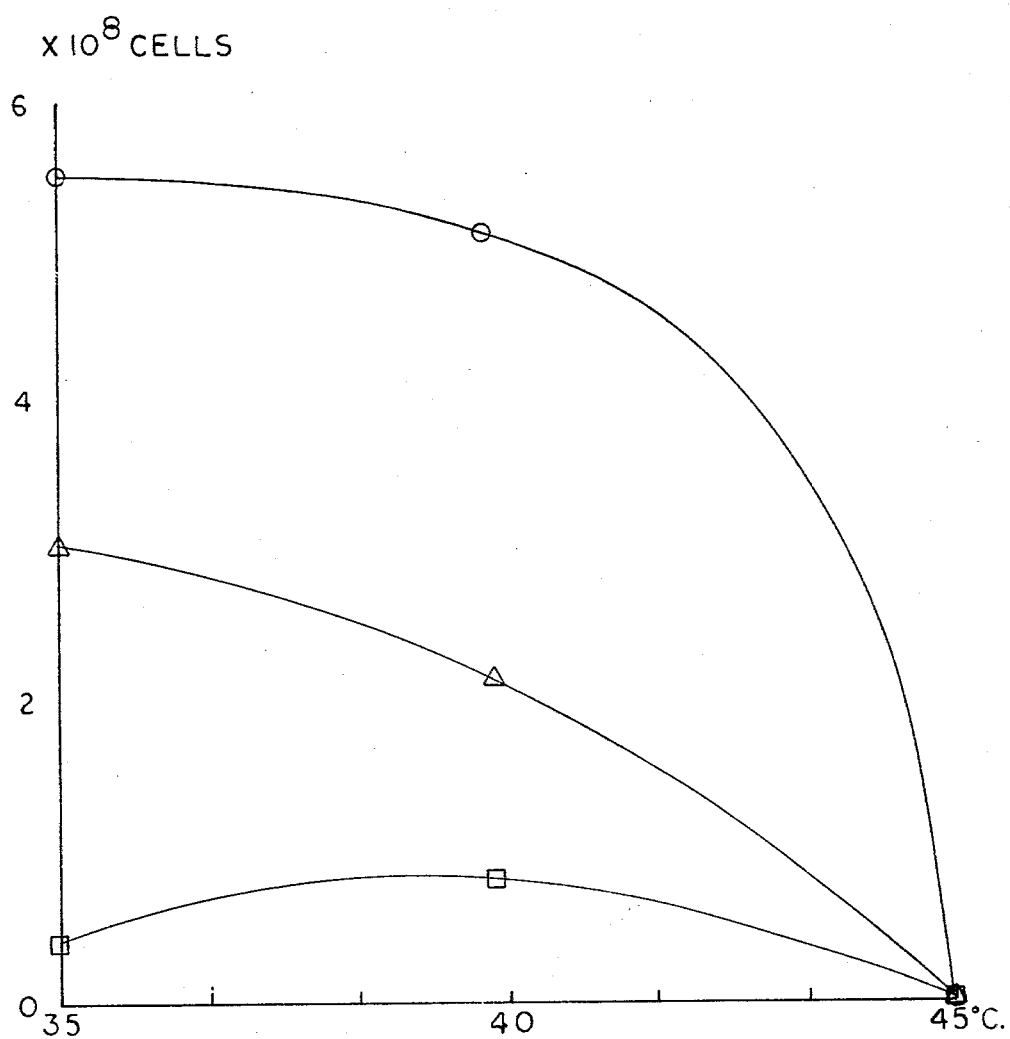
FIG. 3 represents the yeast cell count in the biomass residue after 24 hours at the indicated temperatures of a simultaneous saccharification-fermentation of cellulose according to the method of Gauss et al. after inoculation with an equivalent concentration of cellulose derived from *Trichoderma reesei* QM9414 and identical cell counts of the various yeasts.
Figure 4:
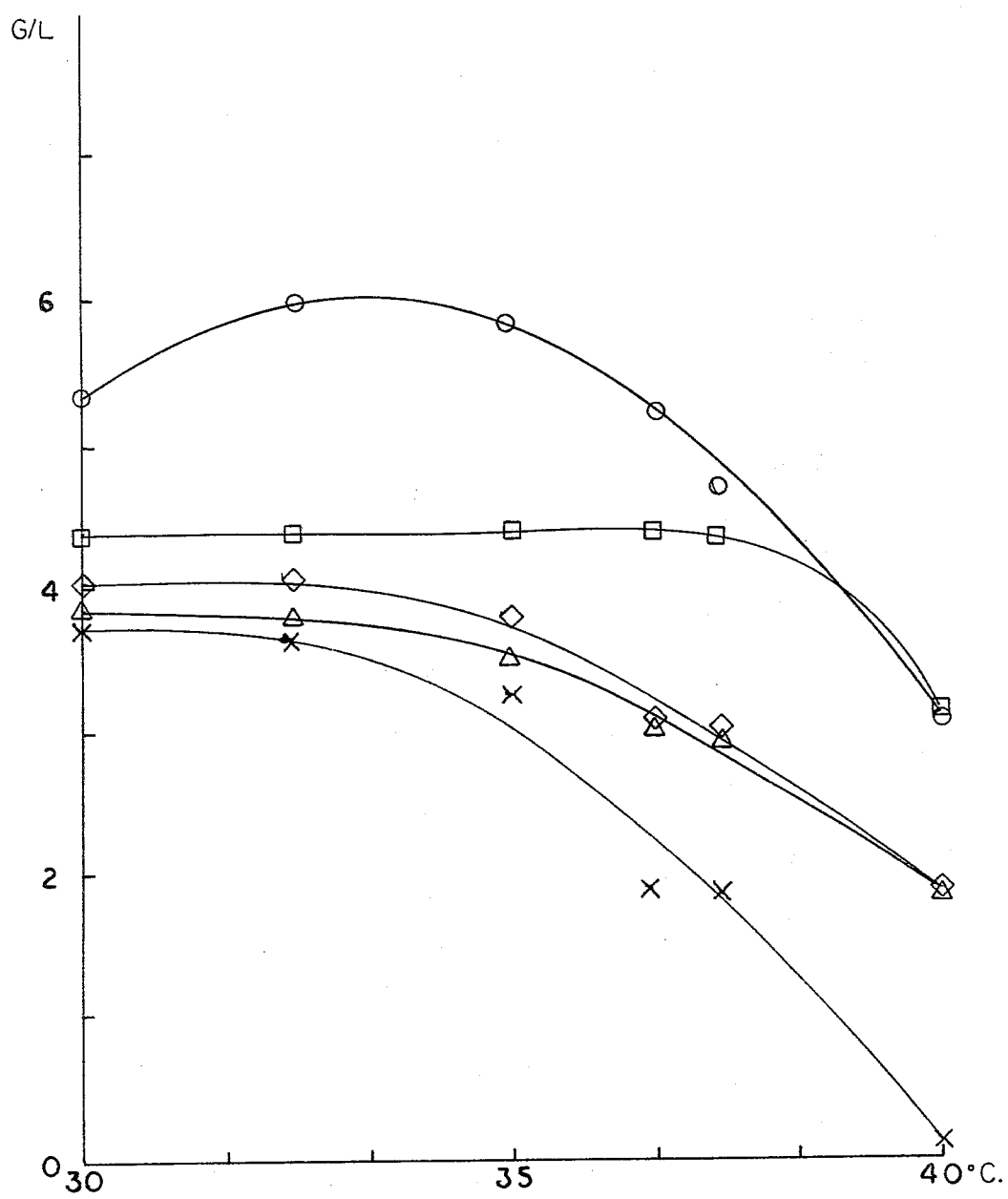
FIG. 4 represents the mass concentration of cell units obtainable after 12 hours of growth of the identified yeast on the glucose-containing nutrient medium as defined above for FIG. 2 at the various temperatures.
Figure 5:
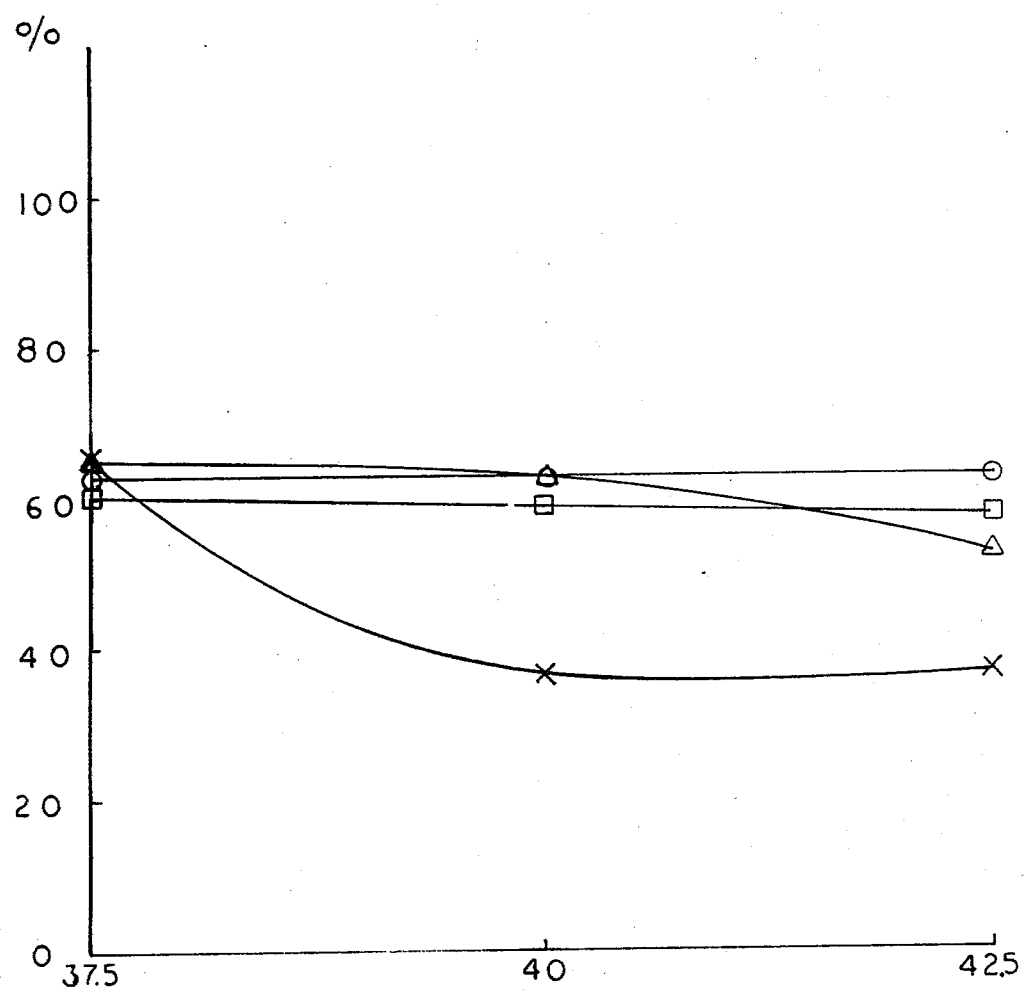

FIG. 5 represents the overall ethanol yield after 24 hours of a simultaneous saccharification-fermentation carried out at various temperatures. The curves indicate that at temperatures of 37.5°–40° C. the yeast *Candida brassicae* ATCC 32196 is about equivalent to the usual *Saccharomyces cerevisiae* and *Saccharomyces carlsbergensis*, however, at temperatures over 40° C. the activity of the yeast remains high with no depletion in alcohol production. Since the simultaneous saccharification-fermentation is an overall exothermic process operated generally at between 37.5° and 40° C. the ability of the yeast to maintain activity at above 40° C. is commercially advantageous because expensive and sophisticated cooling devices are not needed and a partially run-away reaction can be tolerated without loss of alcohol yield.

Fermentation and yeast production is carried out by adding an aqueous slurry of the yeast to a nutrient medium containing:

Glucose—2%
Yeast extract—0.5%
Malt extract—0.5%
Peptone—0.5% with slow to medium agitation (120 r.p.m.) and a 1 v/v/m aeration rate. pH 5.0 is maintained by intermittent addition of standardized reagents. Cells are isolated by centrifugations after 24 hours of growth at 38° C. and the cell cake is used for fermentation of glucose or in a simultaneous saccharification-fermentation reaction as by the method of Gauss et al, U.S. Pat. No. 3,990,944.

We claim:

1. In a process for the manufacture of alcohol from cellulose by the simultaneous addition of cellulase and a yeast to a cellulose-containing material and isolation and recovery of the resulting ethanol, the improvement which comprises using *Candida brassicae* ATCC 32196 as the yeast.

2. In a process for the manufacture of ethanol from fermentable sugars by fermentation, the improvement which comprises using *Candida brassicae*, ATCC 32196 as the yeast.

3. In a process for the manufacture of yeast protein from the growth of a fermentation yeast in a nutrient medium, the improvement of using *Candida brassicae* ATCC 32196 as the yeast.

* * * * *